United States Patent
Feistel et al.

(10) Patent No.: US 8,329,228 B2
(45) Date of Patent: Dec. 11, 2012

(54) SPECIAL EXTRACT AND USE THEREOF FOR INHIBITING THE DEGRADATION OF CYCLIC GUANOSINE MONOPHOSPHATE (CGMP)

(75) Inventors: Björn Feistel, Andernach (DE); Matthias-Heinrich Kreuter, Walenstadt (CH)

(73) Assignee: Finzelberg GmbH & Co. KG, Andernach (DE)

( * ) Notice: Subject to any disclaimer, the term of this patent is extended or adjusted under 35 U.S.C. 154(b) by 0 days.

(21) Appl. No.: 12/518,735

(22) PCT Filed: Dec. 11, 2007

(86) PCT No.: PCT/EP2007/063668
§ 371 (c)(1),
(2), (4) Date: Jan. 12, 2010

(87) PCT Pub. No.: WO2008/071684
PCT Pub. Date: Jun. 19, 2008

(65) Prior Publication Data
US 2010/0119627 A1    May 13, 2010

(30) Foreign Application Priority Data
Dec. 11, 2006    (EP) .................................... 06125821

(51) Int. Cl.
*A61K 36/00*    (2006.01)
(52) U.S. Cl. ..................................................... 424/725
(58) Field of Classification Search .................. None
See application file for complete search history.

(56) References Cited

FOREIGN PATENT DOCUMENTS
WO    WO 03/094943 A1    11/2003

OTHER PUBLICATIONS

Antonio et al, Oral anti-inflammatory and anti-ulcerogenic activities of a hydroalcoholic extract and partitioned fractions of *Turnera ulmifolia* (Turneraceae, Journal of ethnopharmcology 61 (1998) 215-228.*
Suffness, Drugs of plant origin. Methods in cancer research, 1979; XVI: 73-126.*
Alarcon-Aguilar, F.J. et al., "Investigation on the Hypoglycaemic Effects of Extrats of Four Mexican Medicinal Plants in Normal and Alloxan-Diabetic Mice," Phytotherapy Research, Jun. 2002, 16(4), 383-386.
Antonio, M.A. et al., "Oral anti-inflammatory and anti-ulcerogenic activities of a hydroalcoholic extract and partitioned fractions of *Turnera ulmifolia* (Turneraceae)," Journal of Ethnopharmacology, Jul. 1998, 61(3), 215-228.
Arletti, R. et al., "Stimulating property of *Turnera diffusa* and *Pfaffia paniculata* extracts on the sexual behavior of male rats," Psychopharmacology, Mar. 1999, 143(1), 15-19.
Chew et al., "Erectile dysfunction, sildenafil and cardiovascular risk," Med. J. Australia, Mar. 2000, 172(6), 279-283.
Handbuch der Phytotherapie, p. 106, Wiss. Verlagsgesellschaft, Stuttgart, 2003.
http://www.medhost.de/impotenz/sildenafil.html , 2007.
Mullershausen, F. et al., "Direct activation of PDE5 by cGMP: long-term effects within NO/cGMP signaling," J. Cell Biology, Mar. 3, 2003, 160(5), 719-727.
Tharakan, B. et al., "Botanical therapies in sexual dysfunction," Phytotherapy Research, Jun. 2005, 19(6), 457-463.
VitaPlant Study Report sponsored by Finzelberg GmbH entitled: "PDE 5 Inhibitionsstudie in vitro mit Damiana Extrakten," Pharma 063_07_FB_Damiana PDE 5, Swiss Research Institute for Phytopharmaceutical Products, Nov. 12, 2007.
World Health Organization (WHO), "Progress in Reproductive Health Research", 2004, No. 67, 8 pp.

* cited by examiner

*Primary Examiner* — Qiuwen Mi
(74) *Attorney, Agent, or Firm* — Woodcock Washburn LLP

(57) ABSTRACT

A process for the preparation of an extract from a plant of the Turneraceae family, comprising the steps of:
  extracting plant parts with an extractant containing, in addition to water, an organic solvent selected from methanol, ethanol, propanol, isopropanol, acetone and mixtures thereof;
  concentrating the extracts to form a viscous extract;
  enriching the lipophilic substances to form a concentrate.

14 Claims, 5 Drawing Sheets

IC$_{50}$= 1nM

IC$_{50}$= 8µg/ml

IC$_{50}$ = 5μg/ml

Figure 1A:
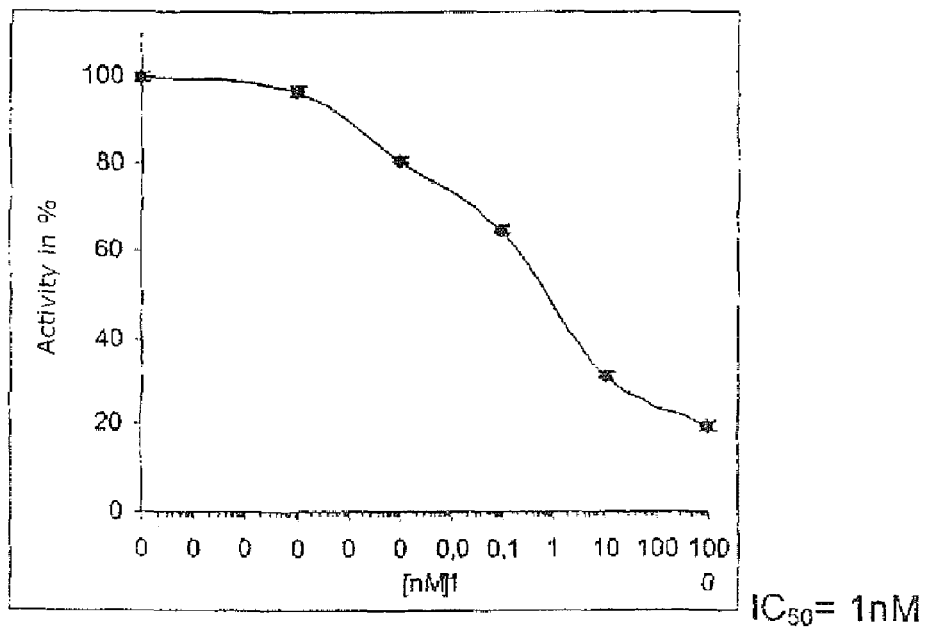

SPECIAL EXTRACT AND USE THEREOF FOR INHIBITING THE DEGRADATION OF CYCLIC GUANOSINE MONOPHOSPHATE (CGMP)

CROSS-REFERENCE TO RELATED APPLICATIONS

This application constitutes entry into the U.S. National Stage of PCT/EP2007/063668, filed 11 Dec. 2007, which in turn claims priority of European Application No. 06125821.6, filed 11 Dec. 2006. Each of these priority applications are incorporated herein by reference for all purposes.

The following invention relates to a process for preparing extracts of a plant from the Turneraceae family, the extracts thus obtained and the use thereof.

The WHO defines the human right relating to sexuality among others as the right to the highest attainable standard of sexual health, and the right to pursue a satisfying, safe and pleasurable sexual life (WHO Progress in Reproductive Health Research 2004; No. 67, pp. 3).

According to a global study, 84 percent of the men state that sexuality is an important part of their lives, and that a satisfying sex life has a positive effect on their perceived quality of life. A large proportion of men from the age of 40 suffer from impaired erection=erectile dysfunction (ED). This term describes the inability to develop or maintain an erection of the penis sufficient for satisfactory sexual performance.

Causes of impaired erection may be organic and/or psychological in nature. Chronic diseases, advancing age, drugs and natural stimulants, such as alcohol and nicotine, can be considered as risk factors, as can stress, partnership conflicts, depressions or fear of failure. The loss of sexual potency strongly shakes the physical, physiological and social self image of men, especially young men. Patients with chronic ED are made uncertain in their sexuality and personality and are to be regarded as being ill.

To understand this clinical picture, the basics of the anatomy of penile erection are necessary: The penis contains the dorsolateral cavernous bodies and the medioventral spongy body, which are sponge-like structures consisting of cavernous spaces. These cavernous spaces are clad with vascular epithelium cells and are supplied with blood through the internal pudendal artery. The blood is drained through the deep dorsal vein of penis.

Also, the influence of physiology has to be considered. Penile erection and detumescence are hemodynamic processes, which are regulated through the relaxation and contraction of the cavernous smooth muscles.

In a resting condition, the sympathetically innerved smooth muscles of the cavernous body arteries are in a contracted state. The blood flow through the cavernous bodies is therefore minimal. Upon sexual stimulation, the parasympathetic activity increases, whereby the arteries dilate, and the blood flow through the cavernous bodies increases. Due to the increase in volume, the draining veins between the cavernous bodies and the tunica albuginea are compressed, and the blood draining is reduced. The consequence of this veno-occlusive mechanism is a rigid erection.

In terms of molecular physiology, the following schematic course occurs: Through nonadrenergic/noncholinergic neurons, sexual stimulation results in the L-arginine-based production of nitrogen monoxide (NO). NO acts as an "endothelium derived relaxing factor". It diffuses into the smooth muscle cells and activates guanylate cyclase therein. This induces the formation of cGMP from GTP. cGMP results in a detumescence of the cavernous smooth muscles. Finally, cGMP is degraded by phosphodiesterase type V (PDE-V) into guanosine monophosphate (GMP) and thus inactivated (Chew et al., Med. J. Aust. 172, 279-283, 2000).

In an ED, too little NO is released relative to the required action in many cases. This is also favored by other disease-related effects, such as vascular lesions or increased NO tolerance. The route via an increase of the endothelially mediated NO production is described for many "remedies", often in connection with an administration of L-arginine as a combination partner.

The relationship between positively tested NO donors (formation of cGMP) and the effect on the inhibition of PDE-V (degradation of cGMP) has not been described.

Now, in order to ensure a stable erection, it also makes sense to selectively disturb the degradation mechanism of cGMP and thus to achieve a longer half life of the cGMP. This degradation is prevented by the phosphodiesterases. In order to be able to substantially avoid side effects, it has proven useful in the past to inhibit the phosphodiesterase type V as selectively as possible, because it occurs almost exclusively in the cavernous bodies while other subtypes, such as PDE-I and PDE-II, occur ubiquitarily in the body. This mechanism of action is known for sildenafil (Chew et al., Med. J. Aust. 172, 279-283, 2000).

In addition to this effect of PDE-V inhibition, a large number of side effects has also been described for this synthetically obtained substance. Thus, sildenafil should not be ingested briefly after a meal or after the consumption of alcohol, because this clearly reduces the effect, and not with hypotension, a known risk of stroke, angina pectoris or cardiac insufficiency either.

Side effects described for sildenafil include a drop in blood pressure, headache, dyspepsia and muscle pain.

Plant formulations are known to have a very narrow range of side effects. In search of aphrodisiacs from nature, one quickly arrives at a wide variety of, in part obscure, "remedies", which have often been employed for centuries. If this topic is considered with limitation to plant preparations, a wide variety of different plants employed and formulations of a wide variety of qualities and efficiencies (plant powder, teas, decoctions, liquid extracts) is still obtained in almost all tribal peoples.

It is the object of the present invention to find a plant effective against ED and to convert their active components to a reproducible extract form. Thus, a therapeutically uniform and effective dose is to be ensured. In contrast to the original plant part, the form of a highly concentrated plant extract is particularly suitable.

Within the scope of a pharmacological in vitro screening, plants that have been employed as aphrodisiacs traditionally were examined in terms of potential PDE-V inhibition. In this screening, a correspondingly active plant family has been found, i.e., the Turneraceae family.

One plant of this genus, *Turnera diffusa*, German designation "damiana", is originally indigenous to the Gulf of Mexico shores and the Caribbean. Traditionally, the dried leaves of *Turnera diffusa* and its varieties have been consumed in the form of dry plant powder, teas or tonics for enhancing the sex drive.

Such a tonic has been described by Arletti et al. in Psycho Pharmacology (143, 1999, pp. 15-19). Thus, a traditional 1:1 fluid proves to be effective in animal tests with sexually sluggish and impotent rats. A relationship in terms of the kind of extract (fluid extract: influence of the ethanol proportion?) or pharmacological mode of action has not been extracted. Tharakan et al. refer to this work in Phytotherapy Research (19, 2005, 457-463).

In Germany, alcoholic-aqueous single extracts from damiana leaves have also been traditionally used pharmaceutically without ever to have furnished scientific evidence in the form of a human study (Handbuch der Phytotherapie, p. 106; Wiss. Verlagsgesellschaft Stuttgart 2003). The Kommission E of the former Bundesgesundheitsamt (German Federal Health Office) arrived at this result as early as in 1989 by presenting a negative monograph.

Therefore, there is still a need for effective plant extracts, especially for treating erectile dysfunction.

This object is achieved by the process according to the invention for the preparation of extracts.

In a completely surprising manner, it has been established that the efficacy of a damiana leaf extract varied from almost inactive to highly active depending on the selected extraction and process parameters for the extracts obtained. It was also unexpected that both extractions with purely hydrophilic solvents (water) and extractions with purely lipophilic solvents (pure ethanol) proved to be unsuitable procedures for achieving a high activity in the pharmacological test system. Medium polar extractants (e.g., ethanol-water mixtures) showed relatively better results.

Therefore, the present relates at first to a process for the preparation of an extract from a plant of the Turneraceae family, comprising the steps of:
  extracting plant parts with an extractant containing, in addition to water, an organic solvent selected from methanol, ethanol, propanol, isopropanol, acetone and mixtures thereof;
  concentrating the extracts to form a viscous extract;
  enriching the lipophilic substances to form a concentrate.

As starting plants, various members of the Turneraceae family are suitable, especially Turnera acaulis, Turnera acuta, Turnera alba, Turnera albicans, Turnera amapaensis, Turnera angustifolia, Turnera annectens, Turnera annularis, Turnera annularis var. conglomerata, Turnera aphrodisiaca, Turnera apifera, Turnera arcuata, Turnera arenaria, Turnera argentea, Turnera arillosa, Turnera armata, Turnera aromatica, Turnera aspera, Turnera asymmetrica, Turnera aturensis, Turnera urantiaca, Turnera aurea, Turnera aurelii, Turnera aurelioi, Turnera bahiensis, Turnera benthamiana, Turnera berneriana, Turnera bernieriana, Turnera etonicaefolia, Turnera blanchetiana var. aequalifolia, Turnera blanchetiana var. capituliflora, Turnera blanchetiana var. subspicata, Turnera blanchettana, Turnera brasiliensis, Turnera brasiliensis var. breviflora, Turnera brasiliensis var. brevifolia, Turnera breviflora, Turnera caatingana, Turnera caerulea var. surinamensis, Turnera callosa, Turnera calyptrocarpa, Turnera candida, Turnera capensis, Turnera capitata, Turnera capitata subsp. intermedia, Turnera caroliniana, Turnera carpinifolia, Turnera castilloi, Turnera chamaedrifolie, Turnera chamaedrys, Turnera chrysocephala, Turnera chrysodoxa, Turnera cicatricosa, Turnera cipoensis, Turnera cistoides, Turnera clauseniana, Turnera coerulea, Turnera collotricha, Turnera concinna, Turnera corchorifolia, Turnera corchoroides, Turnera coriacea, Turnera crulsii, Turnera cuneifolia, Turnera cuneiformis, Turnera curassayica, Turnera dasystyla, Turnera dasytricha, Turnera decipiens, Turnera desvauxii, Turnera dichotoma, Turnera dichotoma var. stenophylla, Turnera dichotoma var. stricta, Turnera diffusa, Turnera diffusa var. aphrodisiaca, Turnera diffusa var. diffusa, Turnera discolor, Turnera dolichostigma, Turnera duarteana, Turnera duarteana var. rotundifolia, Turnera eichleriana, Turnera elegans, Turnera elliptica, Turnera flammea, Turnera foliosa, Turnera frutescens, Turnera frutescens var. latifolia, Turnera gardneriana, Turnera genistoides, Turnera glabra, Turnera glaziovii, Turnera goyazensis, Turnera grandidentata, Turnera grandiflora, Turnera grandifolia, Turnera guianensis, Turnera harleyi, Turnera hassleriana var. lobulata, Turnera hatschbachii, Turnera hatschbachii var. miniata, Turnera hebepetala, Turnera helianthemoides, Turnera hermannioides, Turnera hexandra, Turnera hilaireana, Turnera hilaireana var. lanceolata, Turnera hilaireana var. minor, Turnera hilaireana var. oblongifolia, Turnera hilaireana var. ovatifolia, Turnera hindsiana, Turnera hindsiana subsp. brachyantha, Turnera hirsuta, Turnera hirsutissima, Turnera hirta, Turnera hispidissima, Turnera huberi, Turnera humboldtii, Turnera humifusa, Turnera ignota, Turnera incana, Turnera integrifolia, Turnera joelii, Turnera joellii, Turnera krapovickasii, Turnera lamiifolia, Turnera lanceolata, Turnera leptosperma, Turnera lineata, Turnera longiflora, Turnera longipes, Turnera lucida, Turnera luetzelburgii, Turnera luminosa, Turnera lutescens, Turnera macrophylla, Turnera madagascariensis, Turnera maracasana, Turnera marmorata, Turnera martii, Turnera melanorhiza, Turnera melanorhiza var. latifolia, Turnera melochia, Turnera melochioides, Turnera melochioides var. angustifolia, Turnera melochioides var. arenaria, Turnera melochioides var. genuina, Turnera melochioides var. oblongifolia, Turnera melochioides var. ramosissima, Turnera microphylla, Turnera mollis, Turnera muricata, Turnera nana, Turnera nervosa, Turnera oblongifolia, Turnera obtusifolia, Turnera oculata, Turnera oculta var. paucipilosa, Turnera odorata, Turnera opifera, Turnera orientalis, Turnera ovata, Turnera palmeri, Turnera panamensis, Turnera paniculata, Turnera paruana, Turnera parviflora, Turnera pernambucensis, Turnera peruviana, Turnera pilosula, Turnera pinifolia, Turnera pinnatifida, Turnera pinnatifida var. angustiloba, Turnera pinnatifida var. carnea, Turnera pinnatifida var. lycopifolia, Turnera pohliana, Turnera prance/, Turnera princeps, Turnera pringlei, Turnera procumbens, Turnera pumila, Turnera pumilea, Turnera pumilea var. piauhyensis, Turnera pumileoides, Turnera purpurascens, Turnera racemosa, Turnera ramosissima, Turnera refracta, Turnera revoluta, Turnera riedeliana, Turnera rosea, Turnera rubrobracteata, Turnera rugosa, Turnera rupestris, Turnera rupestris var. frutescens, Turnera salicifolia, Turnera schomburgkiana, Turnera schwackeana, Turnera sedoides, Turnera selloi, Turnera sericea, Turnera serrata, Turnera serrata var. angustifolia, Turnera serrata var. brevifolia, Turnera serrata var. latifolia, Turnera serrata var. schwackei, Turnera setifera, Turnera setosa, Turnera setosa var. entreriana, Turnera setosa var. integrifolia, Turnera sidaefolia, Turnera sidoides, Turnera sidoides subsp. carnea, Turnera sidoides subsp. holosericea, Turnera sidoides subsp. integrifolia, Turnera sidoides subsp. pinnatifida, Turnera sidoides var. angustiloba, Turnera sidoides var. grisebachiana, Turnera sidoides var. herteriana, Turnera sidoides var. hispida, Turnera sidoides var. holosericea, Turnera sidoides var. incisa, Turnera sidoides var. lycopifolia, Turnera simulans, Turnera stachydifolia, Turnera stachydifolia var. flexuosa, Turnera stenophylla, Turnera steyermarkii, Turnera stipularis, Turnera subglabra, Turnera subnuda, Turnera subulata, Turnera surinamensis, Turnera tapajoensis, Turnera tenuicaulis, Turnera thomasii, Turnera tomentosa, Turnera tortuosa, Turnera triglandulosa, Turnera trigona, Turnera trioniflora, Turnera uleana, Turnera ulmifolia, Turnera ulmifolia var. acuta, Turnera ulmifolia var. alba, Turnera ulmifolia var. coerulea, Turnera ulmifolia var. cuneiformis, Turnera ulmifolia var. elegans, Turnera ulmifolia var. elliptica, Turnera ulmifolia var. grandidentata, Turnera ulmifolia var. grandiflora, Turnera ulmifolia var. intermedia, Turnera ulmifolia var. orientalis, Turnera ulmifolia var. velutina, Turnera urbanii, Turnera valleana, Turnera velutina, *Turnera venosa, Turnera villosa, Turnera violacea, Turnera virgata, Turnera viscosa, Turnera waltherioides, Turnera weddelliana, Turnera weddelliana* var. *brachyphylla, Turnera weddelliana* var. *normalis, Turnera whitei, Turnera xanthotricha, Turnera zanthotricha* or *Turnera zeasperma*. A preferred genus is the plants from the genus *Turnera diffusa* WILLD, especially *Turnera diffusa* var. *aphrodisiacs* Urb.

Suitable plant parts include the leaves or herb, in particular, which are employed in a cut or ground form as typical of plant extractions.

Aqueous solutions of water-miscible organic solvents selected from ethanol, methanol, propanol, isopropanol, acetone and mixtures thereof are employed as extractants.

Preferably, the extractant contains the solvent or mixture of solvents in an amount of from 20 to 90%, preferably from 30 to 80%, more preferably from 50 to 70%, by weight. The balance of the extractant is water.

Preferably, the primary extraction is performed exhaustively, wherein the extraction may be performed at an elevated temperature of, for example, 30 to 50° C., preferably 40 to 50° C.

Multistage extractions may also be employed.

Amounts of from 1 to 20 parts by weight, preferably from 6 to 12 parts by weight, of extractant per part by weight of plant parts to be extracted have proven to be particularly suitable.

After the extraction, the extract obtained is concentrated to form a viscous extract. This can be done by methods known to the skilled person, for example, concentration by evaporation under vacuum on a rotary evaporator, thin-film evaporator or plate evaporator.

A critical step for increasing the effectiveness of the extract is a subsequent step for enriching lipophilic substances in combination with the depletion of hydrophilic substances.

A process in which water is added to the viscous extract, the viscous extract is dispersed and the aqueous supernatant is discarded has proven to be particularly suitable. The residue, the so-called extractive precipitate, is separated from insolubles by re-extraction with a mixture of organic solvent and water. The thus obtained extracted substances are concentrated by evaporation, admixed with drying auxiliaries, and dried.

It has been found particularly suitable to select the amount of water for dispersing the viscous extract in such a way that about 2 to 12 parts by weight of the viscous extract is employed per 100 parts by weight of water.

Another process for enriching the lipophilic substances in the concentrate and thus for depleting the hydrophilic substances is a liquid/liquid extraction, by which a partition of the components between water and lipophilic solvent insoluble in water is achieved. The aqueous phase is discarded, and the more lipophilic liquid extract is further employed.

An enrichment of lipophilic extracts can also be achieved by chromatographic methods in which lipophilic components are bound, for example, to RP materials, and the substances not bound are removed before the bound substances are eluted.

The above described process of dispersing the viscous extract in water is particularly preferred.

The preferred embodiment of dispersing yields an extractive precipitate, which is converted to an aqueous solution and re-extracted with an organic solvent of from 30 to 90% by weight selected from methanol, ethanol, propanol, isopropanol, acetone and mixtures thereof. The extractives obtained thereby are separated from insoluble components and concentrated by evaporation to form a viscous (spissum) extract.

Drying auxiliaries are preferably added to an extract according to the invention depleted of lipophilic components, and the thus obtained mixture is dried. Despite of the relatively high co-extracted chlorophyll content in the extract, dry extracts that are readily processed are obtained thereby.

As drying auxiliaries, especially those consisting of polysaccharides, such as gum arabic, xanthan gum etc., and drying auxiliaries based on crystalline cellulose and silicon dioxide have proven suitable.

In a particularly preferred embodiment, from 0.1 to 0.6 parts by weight of gum arabic, from 0.05 to 0.5 parts by weight of microcrystalline cellulose and from 0.01 to 0.1 parts by weight of silicon dioxide are employed as drying auxiliaries per part by weight of the obtained raw extract.

The invention also relates to the extract obtainable by the process according to the invention, especially in the form of a dry extract. This extract exhibits a significant inhibition of human phosphodiesterase V.

Preferably, the $IC_{50}$ value as measured by the process described in the Examples is from 4 to 10 µg/ml.

The invention further relates to the use of the extract according to the invention for preparing a formulation, especially a medicament, for the treatment of conditions in which an increase of the cellular cGMP level by a retarded degradation of cGMP is desired.

Thus, the extract is especially suitable for the preparation of a formulation, especially a medicament, for the treatment of erectile dysfunction, especially to the extent where said erectile dysfunction is caused by an organ-selective deficiency of cGMP.

Figure 1B:
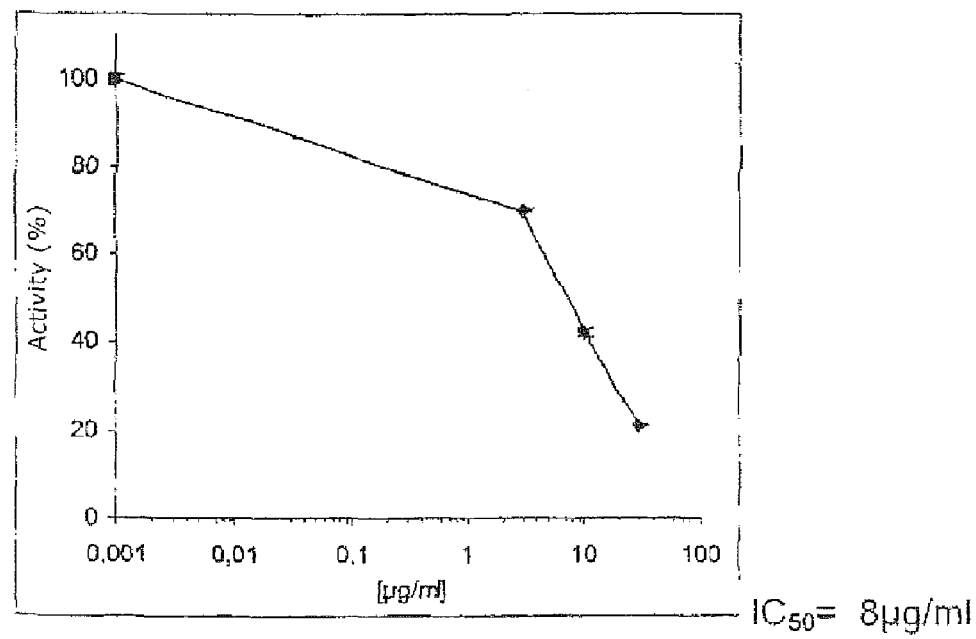
Figure 1C:
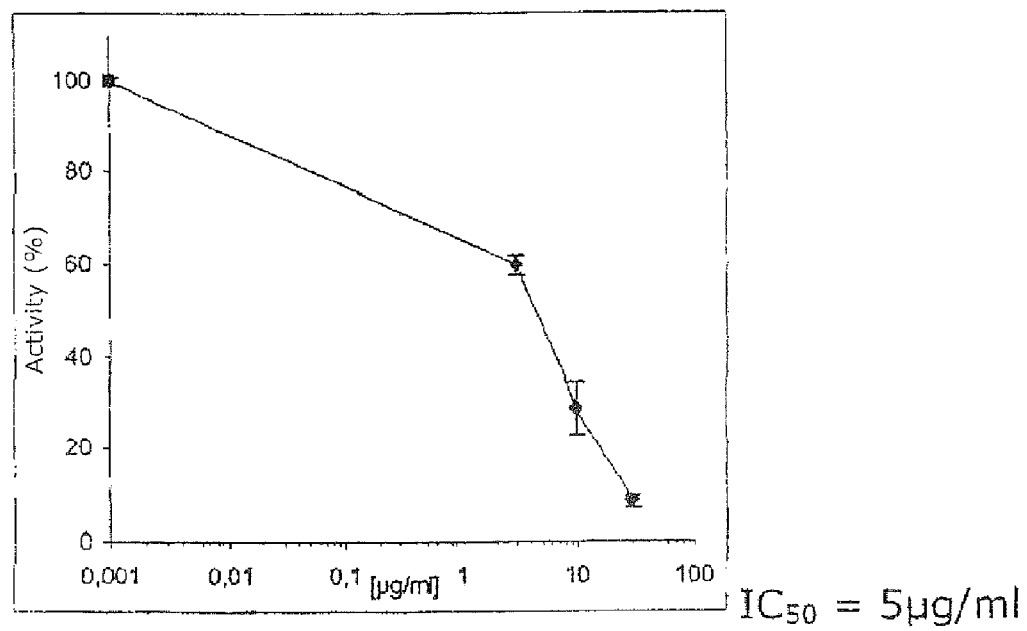

FIG. 1a), FIG. 1b), and FIG. 1c) show the inhibition of PDE-V by the extracts according to the invention as compared to sildenafil according to FIG. 5.

FIG. 1a) shows the inhibition of PDE-V by the sildenafil control.

FIG. 1b) shows the inhibition of PDE-V by the damiana viscous extract according to the invention without drying auxiliaries [extract pattern 5-1].

FIG. 1c) shows the inhibition of PDE-V by the damiana dry extract according to the invention [extract pattern 5-2].

For both extracts, the same amounts of native dry extract equivalent were used for the PDE-V test, and therefore, they are directly comparable.

Figure 2:
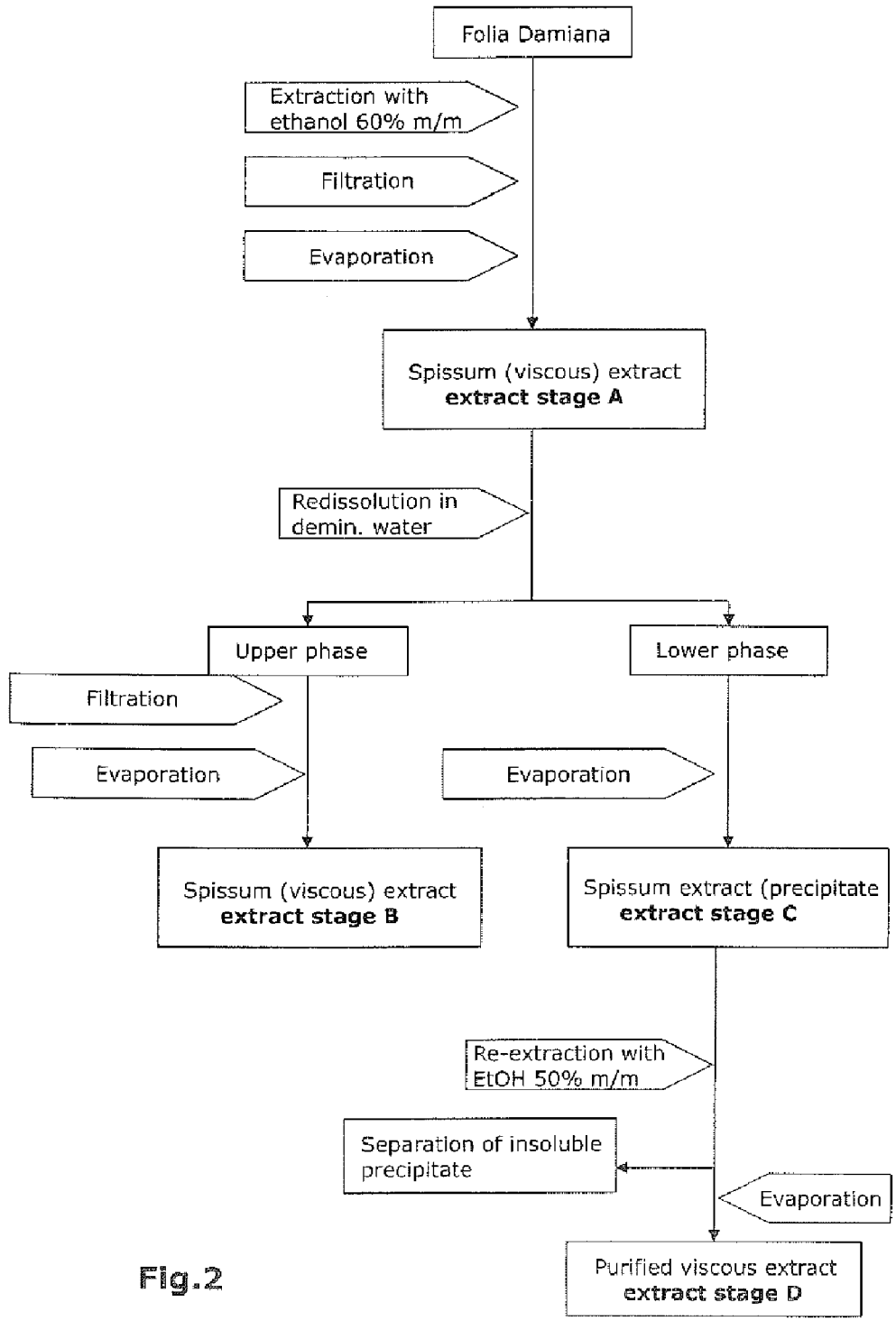

FIG. 2 schematically shows the preparation according to Example 3.

Figure 3:
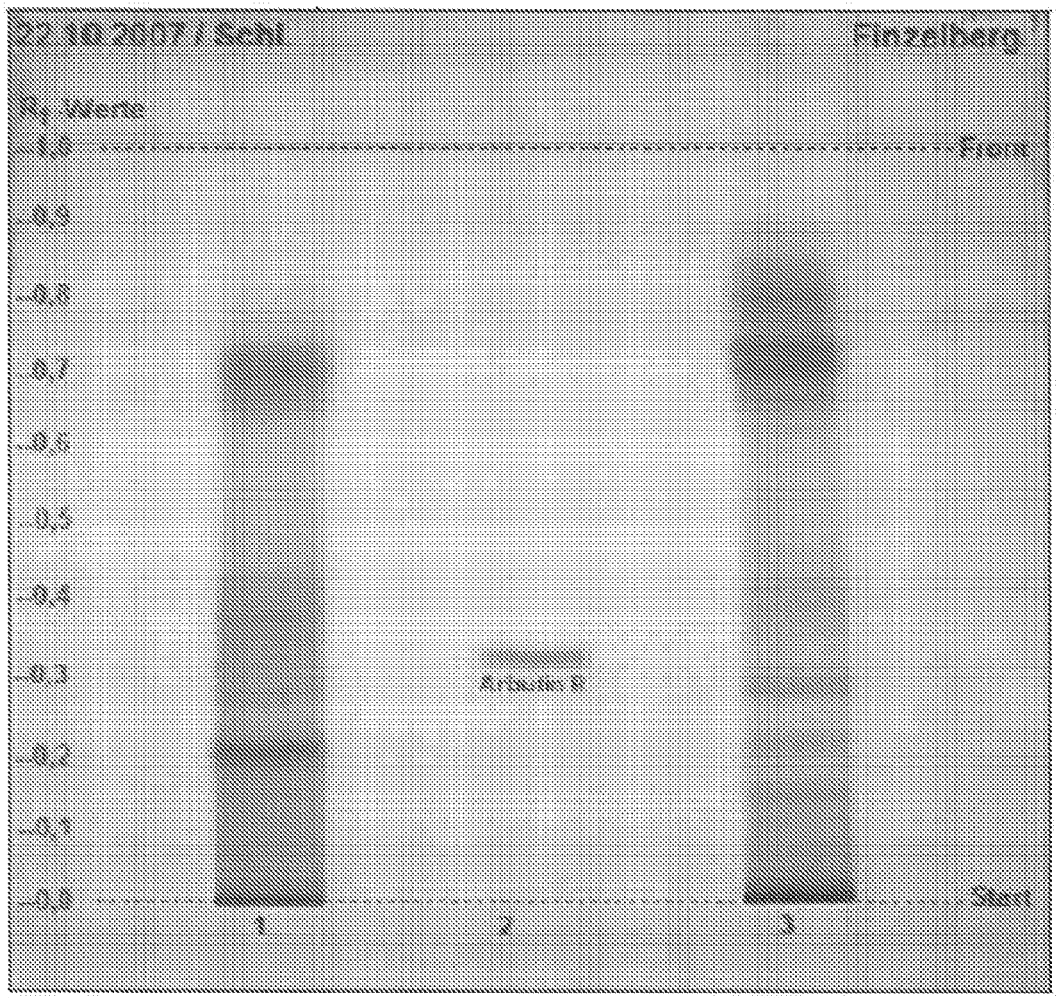
Figure 4:
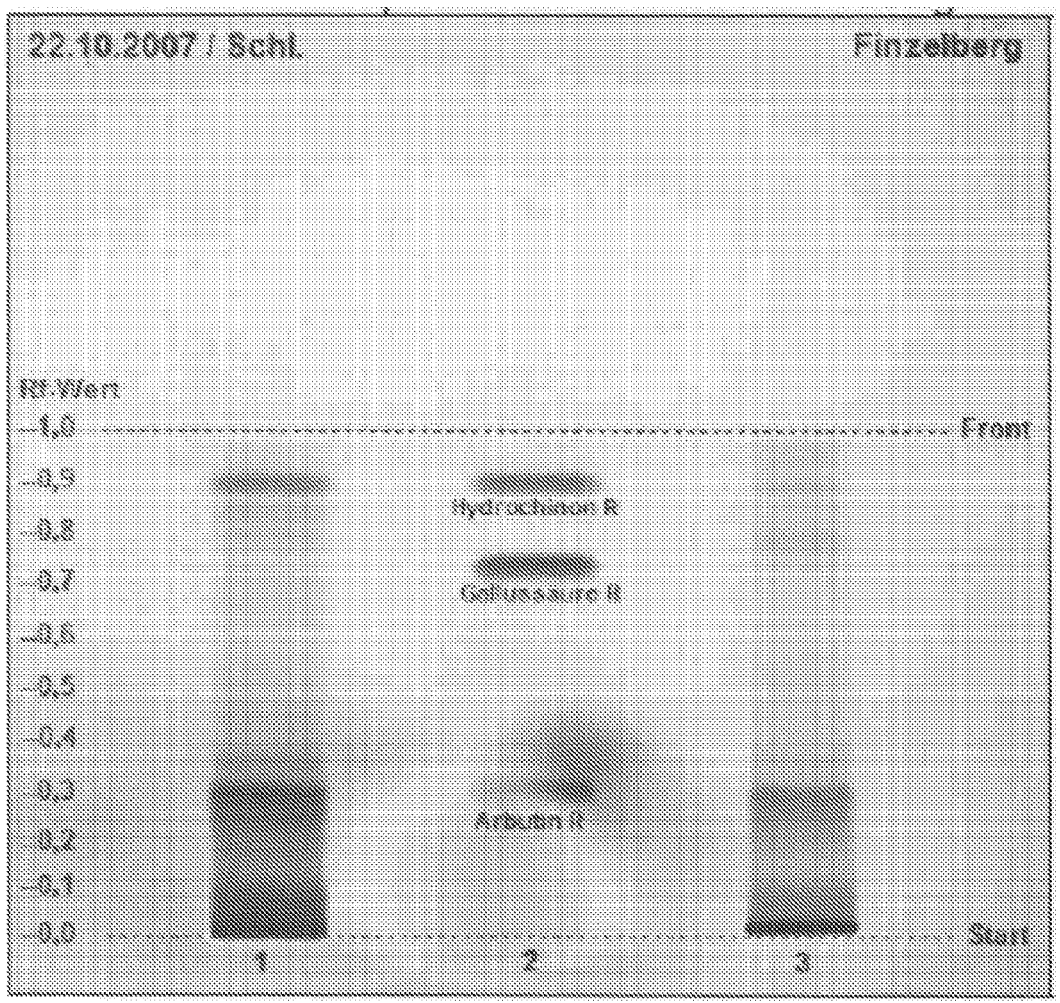

FIG. 3 and FIG. 4 show thin-layer chromatographic analyses of extracts.

The invention is further illustrated by the following Examples.

EXAMPLE 1

Inhibition of PDE-V as a Function of the Extractant

At first, the inhibition of phosphodiesterase V was tested as a function of the solvent concentration. Thus, viscous extracts of folia damiana were prepared with the below stated solvents at a herb-to-extract ratio of 1:12 at 40° C., concentrated, and the extracts were tested for inhibition of PDE-V. The test system was characterized as follows—PDE-V assay (performance according to Schilling, R. J. et al.: Anal. Biochem. 216, 154-158 (1994), and Mullershausen F. et al.: J. Cell Biology 160, 719-727 (2003):

After preincubation of the assay mixture (PDE-V protein content 32 mg/ml) with the extract samples at 24° C. for 15 min, the reaction was started by adding the substrate [$^3$H]-cGMP tracer (0.003 µCi/µl). Subsequently, the assay mixture was incubated at 30° C. for 20 min. Zero checks $t_{(0)}$ were performed without the addition of enzyme.

IC$_{50}$ values were established using a Tritium Scintillation Proximity Assay (PDE-[$^3$H]-cGMP SPA Amersham Biosciences TRKQ 7100) according to the instructions by the manufacturer Amersham. The measured values for the samples were determined from at least two trials per concentration.

The values stated in the following Table were obtained.

TABLE 1

Inhibition of PDE-V as a function of the selected solvent
(test concentration of the extracts 0.3/3.0/30.0 µg/ml;
all based on native dry extract equivalents)

| Extractant | Water | EtOH 30% m/m | EtOH 70% m/m | EtOH 99% m/m |
|---|---|---|---|---|
| IC$_{50}$ µg/ml | >30 * | 15-20 | 10-15 | >30 * |

* no inhibition measurable in this concentration range

EXAMPLE 2

Variation of the *Turnera* Species

Based on these results, it was tried to compare a further differentiation of the *Turnera* species stated in the literature with the commercially available grades of leaves of the Turneraceae. Various species and varieties of *Turnera diffusa* were tested with respect to their PDE-V activities. Thus, extracts from the leaves thereof were extracted with 60% m/m ethanol according to the extraction information of Example 1.

TABLE 2

Inhibition of PDE-V as a function of the *Turnera*
species (test concentration of the extracts 0.3/3.0/30.0
µg/ml; based on native dry extract equivalents)

| | *Turnera* species | | | |
|---|---|---|---|---|
| | T. aphrodisiaca | T. diffusa var. diffusa | T. diffusa var. aphrodisiaca | T. ulmifolia |
| IC$_{50}$ µg/ml | 10-15 | 10-20 | 10-15 | 10-20 |

EXAMPLE 3

Purification of Lipophilic Components

Then, within the scope of further work, it has surprisingly been found that a multistage process conduct starting with a primary extraction with a water-ethanol mixture of 60-80% m/m, followed by concentration by evaporation to form a viscous extract, followed by precipitation in aqueous medium and separation of the supernatant with subsequent re-extraction of the precipitate with a water-ethanol mixture of 40-60% m/m yielded a special extract having an activity increased by several times as compared to the primary extract and an activity increased by about ten times as compared to purely lipophilic extracts in a pharmacological test system for inhibition of phosphodiesterase V.

In a percolator, 20 kg of folia damiana is extracted exhaustively with 60% m/m ethanol at 40° C. The eluates are separated from the plant, filtered and concentrated on a plate evaporator at a maximum of 50° C. to form a solvent-free viscous (spissum) extract. An amount of 5800 g having a dry matter content of 60.3% (=extract stage A) was obtained.

331.7 g of the above viscous extract (=200 g of native dry extract equivalent) was dispersed in demineralized water in portions with stirring. The amount of water is selected in such a way that the dry residue content of the mixture obtained is 10% m/m. This mixture is further stirred for 1 hour and subsequently allowed to stand at room temperature for 12 hours. The precipitated extractive precipitate was separated from the supernatant.

The solution of the supernatant was filtered and concentrated by evaporation to obtain 216 g of viscous extract having an arbutin content of 3.8% (based on native dry extract) and a dry matter content of 60% (=extract stage B). The thus obtained untreated extractive precipitate was homogenized (extract stage C).

The extractive precipitate is subsequently re-extracted with 50% m/m ethanol at a ratio of 1:5. In addition to the soluble extractives, an insoluble precipitate is obtained, which is discarded. The obtained extractives are filtered to clarity and concentrated by evaporation to form an ethanolic-aqueous liquid extract. An amount of 284 g of liquid extract having an arbutin content of 2.2% (based on native dry extract) and a dry matter content of 23% (=extract stage D) was obtained. This is the extract according to the invention. The course of the process is schematically represented in FIG. 2.

TABLE 3

Inhibition of PDE-V as a function of the extraction stages
(test concentration of the extracts 0.3/3.0/30.0 µg/ml;
based on native dry extract equivalents)

| Extract stages | A | B | C | D |
|---|---|---|---|---|
| IC$_{50}$ µg/ml | 15 | 15 | 10 | 4 |

EXAMPLE 4

Dry Auxiliaries

However, the thus obtained liquid extract can neither be concentrated to a homogeneous viscous extract by means of routine methods, nor can it be dried to a powder, because a wide variety of lipophilic substances, such as chlorophyll, is also extracted in this preparation method, which is known to result in precipitations and phase separations in viscous extracts. Only conversion to a dry extract and the grinding thereof can lead to a homogeneous product. Surprisingly, however, the influence of different drying auxiliaries was shown.

While the drying process is sufficiently successful with usual drying auxiliaries, a deterioration or approximate constant effect on the PDE-V inhibition could only be established.

By adding a mixture of an aqueous solution of gum arabic and the auxiliary agent Prosolv™ (silicified microcrystalline cellulose) during the evaporation process, the occurrence of phase separations and precipitates could be successfully prevented, and after concentration to a viscous extract, the obtained mixture of extract and auxiliary could be dried to obtain a free-flowing powder.

In a percolator, 750 kg of folia damiana is extracted exhaustively with 60% m/m ethanol at 45° C. The eluates are separated from the plant, filtered and concentrated on a plate evaporator at a maximum of 50° C. to form a solvent-free viscous (spissum) extract. An amount of 250 kg having a dry matter content of 74.9% was obtained.

1335 g of the above viscous extract (=1000 g of native dry extract equivalent) is dispersed in demineralized water in portions with stirring. The amount of water is selected in such a way that the dry residue content of the mixture obtained is 5% m/m. This mixture is further stirred for 1 hour and subsequently allowed to stand at room temperature for 12 hours. The precipitated extractive precipitate was separated from the supernatant and subsequently re-extracted with 50% m/m ethanol at a ratio of 1:4. Insoluble components are separated off and discarded. The thus obtained extractives are filtered to clarity and concentrated by evaporation to form an ethanolic-aqueous liquid extract. The resulting liquid extract was admixed with the drying auxiliaries in dissolved or suspended form, homogenized and concentrated by evaporation to be free of solvent, and dried under vacuum at 50° C.

TABLE 4

Inhibition of PDE-V as a function of the drying auxiliaries employed (70% native content/30% auxiliaries) (test concentration of the extracts 0.3/3.0/30.0 µg/ml; based on native dry extract equivalents)

| Composition of the damiana extract formulation | Liquid extract without auxiliaries | 70% native/ 25% GA/ 5% PVP | 70% native/ 25% GA/ 5% Prosolv ™ | 70% native/ 25% MD/ 5% Prosolv ™ | 70% native/ 25% PVPP/ 5% Prosolv ™ |
|---|---|---|---|---|---|
| $IC_{50}$ µg/ml | 6 | 7 | 4 | 6 | 6 |

GA = gum arabic
PVP = soluble polyvidone
PVPP = insoluble polyvidone
Prosolv ™ = silicified microcrystalline cellulose
MD = maltodextrin

EXAMPLE 5

Test for Inhibition of PDE-V

The test in a pharmacological test system shows that the process steps and process parameters according to the invention can yield a special extract that is characterized by an activity towards phosphodiesterase V that is increased by several times as compared to conventional extracts. The invention additionally enables the conversion of the obtained liquid extract to a storage-stabilized dry extract.

In a percolator, 750 kg of folia damiana is extracted exhaustively with 60% m/m ethanol at 45° C. The eluates are separated from the plant, filtered and concentrated on a plate evaporator at a maximum of 50° C. to form a solvent-free viscous (spissum) extract. An amount of 250 kg having a dry matter content of 74.9% was obtained.

2003 g of the above viscous extract (=1500 g of native dry extract equivalent) is dispersed in demineralized water in portions with stirring. The amount of water is selected in such a way that the dry residue content of the mixture obtained is 5% m/m. This mixture is further stirred for 1 hour and subsequently allowed to stand at 4° C. for 12 hours. The precipitated extractive precipitate was separated from the supernatant and subsequently re-extracted with 50% m/m ethanol at a ratio of 1:1. Insoluble components are separated off and discarded. The thus obtained extractives are filtered to clarity and concentrated by evaporation to form an ethanolic-aqueous liquid extract. An amount of 8900 g (41% dry matter content) of lipophilic liquid extract (=extract pattern 5-1) was obtained.

The resulting liquid extract was proportionally admixed with the drying auxiliaries gum arabic (25%) and Prosolv™ (5%) in dissolved or suspended form, homogenized and concentrated by evaporation to be free of solvent, and dried under vacuum at 50° C. (extract pattern 5-2).

The test in the PDE-V assay yielded the following $IC_{50}$ concentrations (all values based on native dry extract equivalents):
Extract pattern 5-1=8 µg/ml
Extract pattern 5-2=5 µg/ml The graphical evaluation of this PDE-V inhibition as compared to sildenafil is represented in FIG. 1.

EXAMPLE 6

Comparative Extract

At first, a comparative extract according to Arletti et al. was prepared. Thus, leaves were macerated with 30% (v/v) ethanol at room temperature over night. The extractant was separated off, and the residue squeezed out. The squeezed-out liquid was combined with the extract, followed by concentration to form a dry extract and redissolution to form a fluid extract (1:1).

EXAMPLE 7

Thin-Layer Chromatographic Analysis

The Arletti extract according to Example 6 and the extract according to Example 3 of the invention were examined by thin-layer chromatography.

FIG. 3 shows a chromatographic examination for hydroquinone derivatives (silica gel 60 $F_{254}$, anhydrous formic acid:water:ethyl acetate (6:6:88, v/v/v)) after vapor treatment with an ammonia solution. Lane 1 shows the Arletti extract, and lane 3 shows the extract according to the invention.

It is found that the Arletti extract has a higher content of hydrophilic substances, while this content is low for the extract according to the invention.

FIG. 4 shows a thin-layer chromatographic examination for polar components (silica gel 60 $F_{254}$, dichloromethane:acetic acid:methanol:water (50:25:15:15 v/v/v/v), spray reagent: anisaldehyde). Lane 1 shows the Arletti extract, and lane 3 shows the extract according to the invention. The extract according to the invention is found to have a higher lipophilic content.

EXAMPLE 8

Comparison of PDE-V Inhibition

The extract according to Example 6 (Arletti) and the extract according to the invention were tested in concentrations of 1, 3, 10, 30 and 60 µg/ml in a PDE-V assay. Thus, PDE-V (protein content 13.5 µg/ml) was preincubated with the extracts at 24° C. for 10 min. Subsequently, the reaction was started by adding $^3$H-GMP (0.003 µCi/µl). The assay mixture was incubated at 30° C. for 20 min. Zero checks were performed without the addition of PDE-V. The $IC_{50}$ values were established using a Tritium Scintillation Proximity Assay (PDE-[$^3$H]-cGMP; Amersham Biosciences TRKQ 7100) according to the instructions by the manufacturer.

The measured values for the samples were determined from two trials and are stated as mean values with the respective deviation from the mean. The dose-dependent reduction of the enzyme activity under the action of the respective sample or reference substance is expressed in a percent dose-effect curve. The $IC_{50}$ values (sample concentration that causes 50% inhibition of the maximum enzyme activity) were determined with the program GraphPad Prism (Version 4, GraphPad Software Inc., San Diego, Calif., USA).

Comparative extract according to Example 6: $IC_{50}$=18.5 µg/ml (95% confidence interval: 17.63 to 19.32 µg/ml).

Extract according to the invention: $IC_{50}$ 2.5 µg/ml (95% confidence interval: 2.13 to 2.86 µg/ml).

To achieve 50% inhibition of the enzyme PDE-V, a clearly lower amount of substance is needed from the extract according to the invention. The extract according to the invention is stronger by a factor of 7.4.

The invention claimed is:

1. A process for the preparation of an extract from a plant of the Turneraceae family, comprising the steps of:
   extracting plant parts with an extractant containing, in addition to water, an organic solvent selected from methanol, ethanol, propanol, isopropanol, acetone and mixtures thereof;
   concentrating the extracts to form a viscous extract;
   enriching the lipophilic substances to form a concentrate by dispersing the viscous extract in water and separating and discarding the aqueous supernatant to obtain an extractive precipitate, re-extracting the extractive precipitate and separating undissolved substances from dissolved extractives.

2. The process according to claim 1, wherein said dispersing yields an extractive precipitate, which is converted to an aqueous solution and re-extracted with an organic solvent of from 30 to 90% by weight selected from methanol, ethanol, propanol, isopropanol, acetone and mixtures thereof, and the extractives soluble in this mixture of solvents are separated from undissolved components and recovered.

3. The process according to claim 1, wherein said dispersing yields an extractive precipitate, which is converted to an aqueous solution and re-extracted with from 40 to 60% by weight ethanol, and the extractives soluble in this mixture of solvents are separated from undissolved components and recovered.

4. The process according to claim 1, wherein said plant parts are leaves or herb, the leaves or herb being extracted in a cut or ground form.

5. The process according to claim 1, wherein said extractant contains said organic solvent in an amount of from 20 to 90 by weight.

6. The process according to claim 5, wherein said extractant contains said organic solvent in an amount of from 50 to 70%, by weight.

7. The process according to claim 1, wherein from 1 to 20 parts by weight of extractant is employed per part by weight of plant parts to be extracted.

8. The process according to claim 7, wherein from 6 to 12 parts by weight of extractant is employed per part by weight of plant parts to be extracted.

9. The process according to claim 1, wherein the obtained concentrate is admixed with drying auxiliaries, and the mixture obtained is dried.

10. The process according to claim 9, wherein said drying auxiliaries are selected from polysaccharides, crystalline celluloses, and/or silicon dioxides.

11. The process according to claim 9, wherein from 0.1 to 0.6 parts by weight of gum arabic, from 0.05 to 0.5 parts by weight of microcrystalline cellulose and from 0.01 to 0.1 parts by weight of silicon dioxide are employed per part by weight of extractives obtained.

12. An extract obtained from the process according to claim 1.

13. The extract according to claim 12, wherein said extract causes inhibition of human phosphodiesterase V (PDE-V).

14. An extract obtained from the process according to claim 9.

* * * * *